United States Patent
Belikan et al.

(10) Patent No.: US 6,391,000 B1
(45) Date of Patent: May 21, 2002

(54) MEANS FOR SUPPLYING A MEDICAL INSTRUMENT WITH RINSING FLUID

(75) Inventors: Thomas Belikan, Knittlingen; Michael Lamprecht, Karlsruhe; Gunter Rentschler, Muenzesheim, all of (DE)

(73) Assignee: Richard Wolf GmbH, Knittlingen (DE)

( * ) Notice: Subject to any disclaimer, the term of this patent is extended or adjusted under 35 U.S.C. 154(b) by 0 days.

(21) Appl. No.: 09/505,218

(22) Filed: Feb. 16, 2000

(30) Foreign Application Priority Data

Feb. 22, 1999 (DE) ........................................ 199 07 594

(51) Int. Cl.⁷ ............................................. A61M 31/00
(52) U.S. Cl. ........................... 604/65; 604/147; 604/245
(58) Field of Search ........................ 604/19, 27, 30–34, 604/65, 67, 140, 147, 118, 123, 131, 245; 128/DIG. 12, DIG. 13

(56) References Cited

U.S. PATENT DOCUMENTS

| | | | | |
|---|---|---|---|---|
| 4,276,023 A | * | 6/1981 | Phillips et al. | ................ 466/85 |
| 5,328,478 A | * | 7/1994 | McVay | |
| 5,464,391 A | * | 11/1995 | DeVale | |
| 5,563,584 A | * | 10/1996 | Rader et al. | ................ 340/618 |
| 5,810,765 A | * | 9/1998 | Oda | .............................. 604/31 |
| 6,149,621 A | * | 11/2000 | Makihara | ..................... 604/27 |
| 6,280,408 B1 | * | 8/2001 | Sipin | ........................... 604/65 |

FOREIGN PATENT DOCUMENTS

| | | |
|---|---|---|
| DE | 92 07 907 | 8/1993 |
| EP | 075 153 | 3/1983 |

* cited by examiner

*Primary Examiner*—Sharon Kennedy
*Assistant Examiner*—Catherine Serke
(74) *Attorney, Agent, or Firm*—Cohen, Pontani, Lieberman & Pavane

(57) ABSTRACT

With this device the rinsing fluid is located in a container which may be set under pressure with a gas and into which pressurised gas via a cannula may be introduced and from which rinsing fluid may be removed via another cannula. The respective filled condition of the container is acquired with a sensor, wherein the temporal course of the gas pressure in the container or of the gas flow into the container is measured and on ascertaining a gas pressure fall or gas flow rise after points in time specific to the system the means may be deactivated.

5 Claims, 3 Drawing Sheets

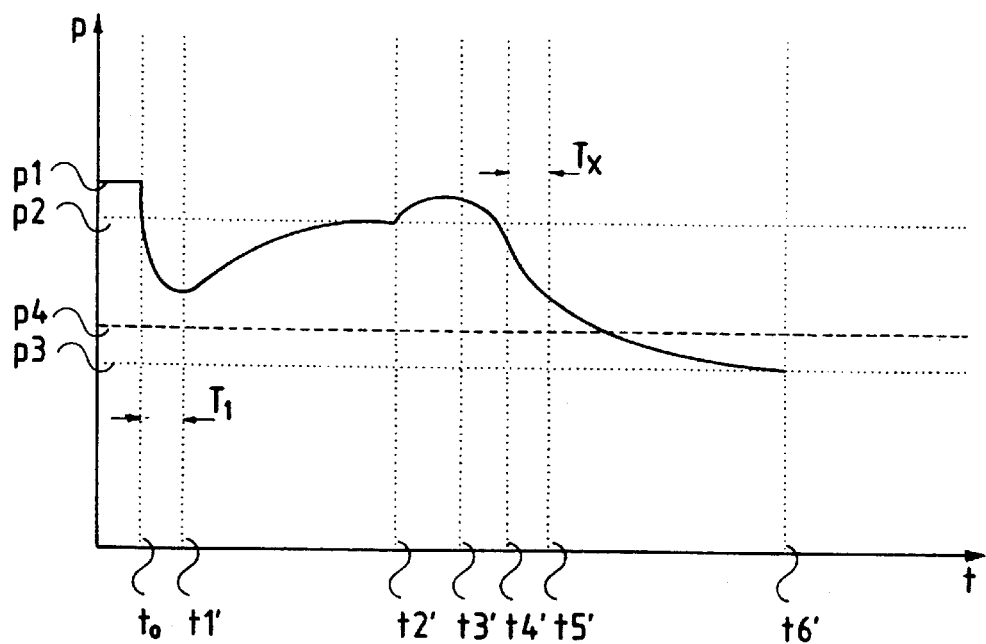
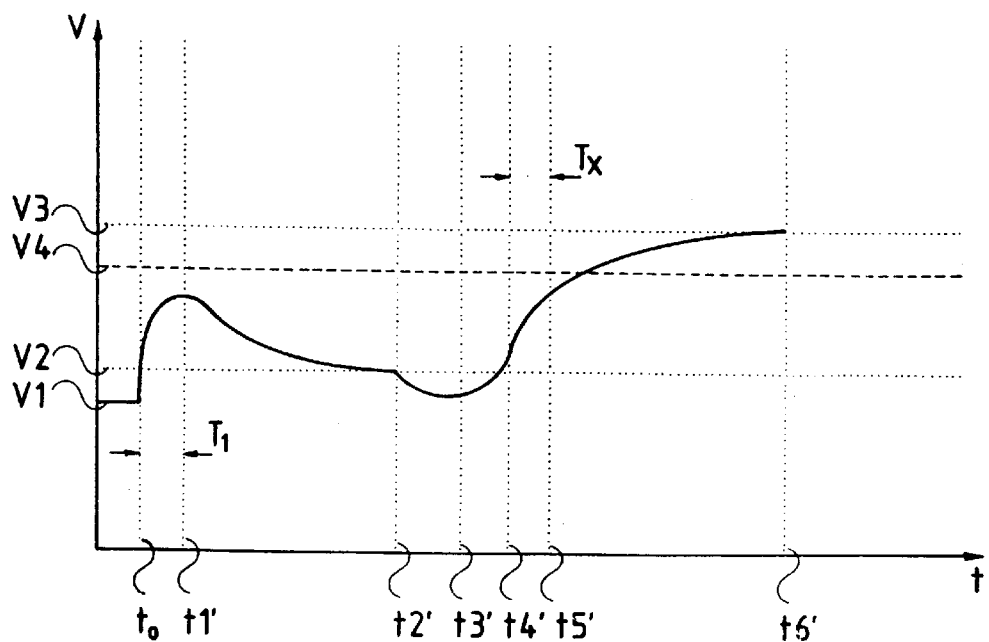

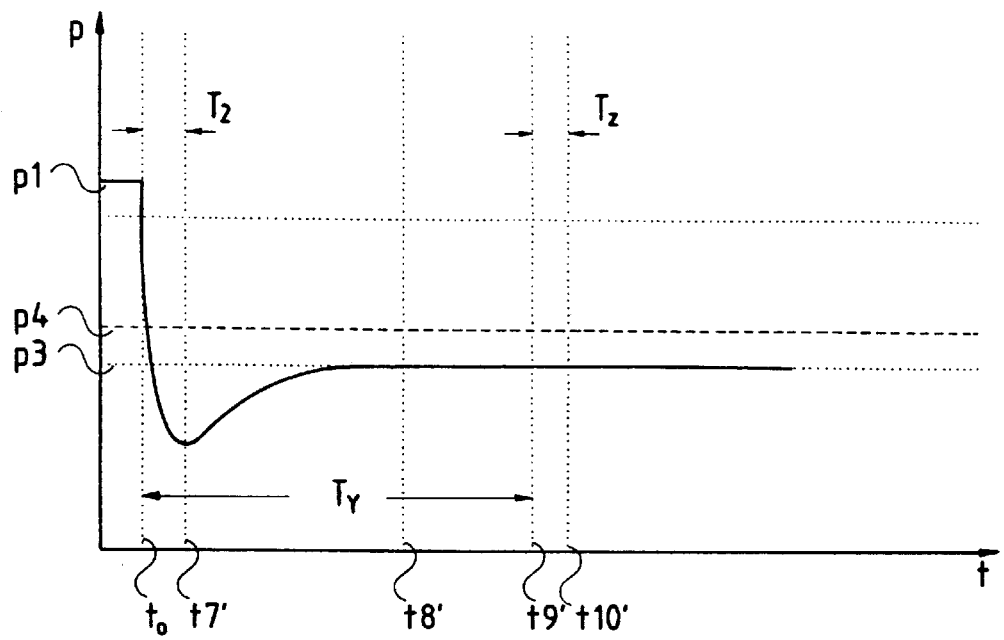
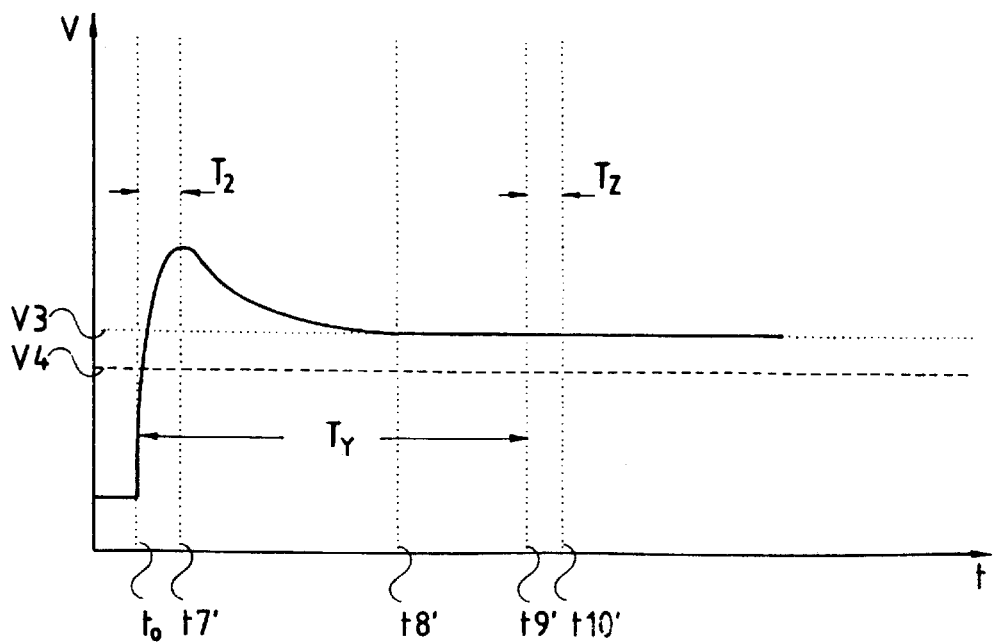

MEANS FOR SUPPLYING A MEDICAL INSTRUMENT WITH RINSING FLUID

BACKGROUND OF THE INVENTION

The invention relates to a means for supplying a medical instrument with rinsing fluid which is located in a container which can be put under pressure with a gas and into which two cannulas of differing lengths are inserted, wherein a short cannula can be connected via a gas conduit and a first valve to a pressurized gas source in order by way of actuation of the means at a point in time t0 to put the container under pressure by way of opening the first valve and forcing fluid from the container into a fluid conduit leading to the instrument. For deactivating the means, the fluid flow to the instrument can be interrupted by way of closing a second valve in the fluid conduit, and the pressurized gas supply to the container can be interrupted by way of closing the first valve. A sensor is provided with which the degree of filling of the container may be acquired and via which given an empty container or one which has become empty the rinsing procedure can be automatically turned off.

With TEM (transanal endoscopic microsurgery) it is necessary to unfold the rectum with $CO_2$ gas and when required to rinse it, in order for example to rinse free the soiled optics window of an endoscope with a sterile salt solution as a rinsing fluid. The rinsing fluid is located in a container designed as a rinsing bottle, which may be impinged by pressure with the $CO_2$ gas in order to be able to force the rinsing fluid out of the container up to the instrument. For this, for example, two cannulas are punctured through a lid or closure of the container filled with salt solution and the one cannula is connected to the pressurised gas source via a valve and the other cannula is connected to the body cavity of a patient via an endoscope or trocar sleeve.

In the course of the application it may occur that so much rinsing fluid is used that the fluid level in the container sinks below the opening of the cannula for the removal of the rinsing fluid, by which means $CO_2$ gas gets into the body cavity and here may lead to a dangerous increases in pressure if the gas supply is not stopped in time. There are already a few devices with measures for monitoring the emptying of the container and for switching off the gas supply into the body cavity with an empty container or one which has become empty.

From the German Utility Model DE-92 07 907 U there is for example known a means with a float in the connection fittings, equipped with the cannulas, for the container or the rinsing bottle. With this the float may occlude the connection to the body cavity when the container has become empty. This principle may also be applied with the use of a suction/rinsing pump. Such means functioning with a float however require a particular connection fitting which contains the specially formed float. It is clear that this is complicated with respect to design and is therefore expensive. Furthermore for such connection fittings materials which are particularly resistant to salt solution such as stainless steel or also titanium must be used. Also such means are not optimal with respect to the hygenic demands. As a further disadvantage is also the fact that known connection fittings are complicated in their handling, and in particular when the user must first remove the closure from the rinsing means container and then must introduce and screw tight the fitting with the float means.

In the previously mentioned utility model measuring electrical solutions with position or limit value sensors are also mentioned. Apart from the costs of acquiring such optical, acoustic or capacitive sensors, means equipped with such sensors are to be seen as critical with respect to their reliability since there are numerous sources of error which cannot be excluded or only at a considerable expense. Thus, for example, the used containers or rinsing bottles have to some part extremely different wall thicknesses which may lead to errors in measurement. Furthermore, the containers often have scratches caused by their transport to the location of application, which at least with optical and capacitative sensors likewise cause errors in measurement. Particularly with optical position sensors it is also the case that these may only function without problem when they are not changed in position, which may not be ensured with every case of application. With an optical sensor the case may also arise in which a formation of drops in an already empty container is interpreted as if there were sufficient fluid present. An arrangement unchangeable in position must also be guaranteed with capacitative position sensors, since for example a change in distance of the sensor to the container will change and falsify the measuring results which are capacitatively changed. Concluding one may say of these solution principles that the position sensor for application of the manner concerned here is not suitable for the practical application, even disregarding the fact that apart from the costs of the sensor the technical expense for eliminating possible sources of error are unacceptably high.

A possible solution of the previously mentioned problems may lie in selecting the cannula diameters so small that also with an empty container and unchanged gas supply into the container and further into the body cavity, with a great probability no physiologically unacceptably high pressure would arise or no unacceptably high gas volume would get into the body cavity. With this type of flow limitation however no optimal rinsing properties arc to be achieved and by way of the gas flow which is not finished when the container has become empty there remains further a risk to the patient.

SUMMARY OF THE INVENTION

By way of the invention the cited disadvantages are to be elliminated. Thus in particular there is to be specified a means which with respect to its construction is inexpensive and with respect to its application is very simple. Furthermore the means is to be extremely secure in its function and is to offer the possibility, with an emptying of the container, of having an automatic stoppage of any gas supply to the instrument securely guaranteed and it is also prevented that containers which are inadvertently empty are put into operation.

For solving this object the initially mentioned means according to a first embodiment is formed such that the sensor is a pressure sensor acquiring the present gas pressure in the container, that in a case A on starting operation of a container sufficiently filled with rinsing fluid the temporal course of the gas pressure in the container can be acquired by way of the sensor and on ascertaining a gas pressure fall during a fixed evaluation time duration Tx the means can be deactivated. Alternatively in a case B on starting operation of an insufficiently filled or empty container the temporal course of the gas pressure in the container can be acquired by way of the sensor and after completion of a predetermined time duration Ty on ascertaining a pressure which during a fixed evaluation time duration Tz runs constant below a predetermined pressure limit value the means can be deactivated.

Another principle for solving the set object is characterised in that the sensor is a flow sensor acquiring the present gas flow in the container, that in the case A on starting operation of a container sufficiently filled with rinsing fluid the temporal course of the gas flow in the container can be acquired by way of the sensor and on ascertaining a gas flow fall during a fixed evaluation time duration Tx the means can be deactivated and that alternatively in a case B on starting operation of an insufficiently filled or empty container the temporal course of the gas flow in the container can be acquired by way of the sensor and after completion of a predetermined time duration Ty on ascertaining a gas flow which during a fixed evaluation time duration Tz runs constant below a predetermined flow limit value, the means can be deactivated.

There is provided an evaluation and control unit to which the sensor is connected and in which the output signals delivered by the sensor mathematically by differentiation may be evaluated by way of a measuring algorithm with respect to the criteria negative gradient of the gas pressure, positive gradient of the gas flow as well as constant remaining values of the gas pressure and gas flow. The mentioned unit then with the persistence of one of these four criteria over a respective predetermined evaluation time duration Ty or Tz will control the second valve for the purpose of closing or blocking the connection from the container to the instrument.

Usefully the means may be activated by actuating a foot switch which via the control and evaluation unit is in connection with an alarm device which on starting operation of an empty container with the foot switch actuation may be set into operation so that the user is immediately made aware of the fact that he must direct his attention to the container and check this whether the container is empty and is to be replaced with one filled with rinsing fluid.

Otherwise in the gas conducting leading branch between the pressurised air source and the short cannula there is connected a throttle with which the flow-through resistance of this gas conducting branch may be so adapted to the flow-through resistance of the conducting branch beginning with the long cannula and conducting rinsing fluid, that there arises a defined pressure drop and an optimisation of the measurement signal outputted by the sensor may be achieved.

BRIEF DESCRIPTION OF THE DRAWINGS

The invention is hereinafter described by way of embodiment examples shown in the drawings. There are shown:

FIG. 2: the temporal course of the pressure acquired by the pressure sensor with a container initially sufficiently filled with rinsing fluid;

FIG. 3: the temporal course of the gas volume flow acquired by a flow sensor with a container initially sufficiently filled with rinsing fluid;

FIG. 4: the temporal course of the pressure acquired by a pressure sensor according to FIG. 2 with a starting operation of an empty container; and FIG. 5: the temporal course of the gas volume flow acquired by the flow sensor according to FIG. 2 on starting operation of an empty container.

DETAILED DESCRIPTION OF THE INVENTION

Figure 1:
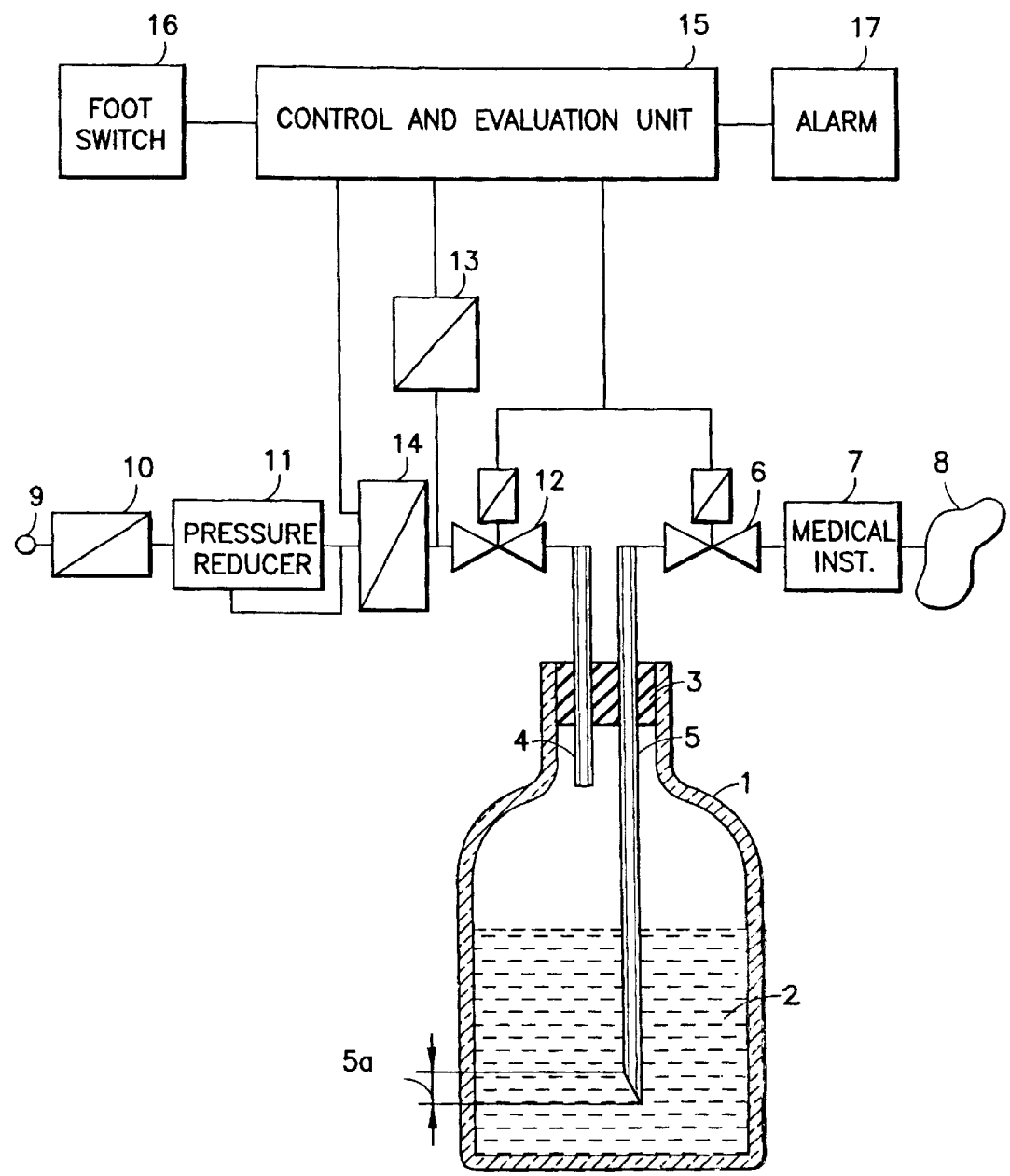
FIG. 1: the block diagram of a means according to the invention.

With the means shown in FIG. 1 the container 1 is filled with rinsing fluid 2 and is provided with a lid or closure 3 through which two cannulas are pierced, and specifically a short cannula 4 for the supply of gas into the container and a long cannula 5 via which with a suitable gas pressure impingement of the container, rinsing fluid 2 via an opened electromagnetic valve 6 is forced to a medical instrument 7 and further into the body cavity 8 of a patient. The two cannulas may furthermore also be grouped together coaxially in the known manner to a cannula set as a constructional unit.

$CO_2$ as coming from a pressurised gas source 9 via a throttle 10, a pressure reducer 11, an electromagnetic valve 12 and the cannula 4 gets into the upper space of the container 1 which is free of rinsing fluid. To the gas conduit between the pressure reducer 11 and the valve 12 there is connected a pressure voltage transducer as a pressure sensor 13. This and where appropriate also the throttle 10 are done away with and are replaced by a flow sensor 14 in the connection between the pressurised gas source 9 and the valve 12 if the means is not to function with a pressure evaluation, but evaluation of the gas volume flow or gas flow.

In a control and evaluation unit 15 there is placed a program with control and measuring algorithms for the operation of the means, the processing of the electrical signals coming from the sensor 13 or 14 and the control of the valves 6, 12 via electrical leads. To this unit 15 there is furthermore connected a foot switch 16 for starting operation of the means and an alarm device 17 which is controlled by the unit 15 and for example raises the alarm when the container 1 has become empty or when inadvertently an empty container has been connected to the means.

On rinsing with an adequately filled container, thus when the cannula 5 protrudes suitably deeply into the rinsing fluid, there results the pressure course shown in FIG. 2. At the entrance of the valve 12 there exists a gas pressure P1 limited by the pressure reducer 11. In order then to be able to rinse, the user by way of actuating the switch 16 opens the valves 6, 12 simultaneously. Since at this point in time t0 the container 1 is initially without pressure the pressure sensor 13 initially registers a reduction in pressure, wherein the pressure at t1' will reach a minimum, which otherwise also according to size and filling of the container may lie lower or higher, but is not evaluated as a criterium for an empty container. The acquisition of the pressure although already begins at t0, the actual evaluation of the pressure which e.g. periodically or in cylces is determined every 10 ms begins however after a time interval T1 at t1', wherein one presupposes that the pressure minimum independently of the size of the container 1 and of the filled condition in the container in each case will be achieved at the latest at t1'. The pressure minimum could, with respect to the pressure course according to FIG. 2, in principle also be reached before the point in time t1'.

In any case from this point in time t1' essentially the pressure build-up in the container 1 begins until the maximum rinsing pressure P2 determined by the complete through-flow resistance of the components of the means and the conduit connections.

If then in the further course of the rinsing procedures the level of the rinsing fluid 2 in the container reduces so much that the straight, or according to FIG. 1 chamfered lower end in the region 5a of the cannula 5 partly begins to get free, from this point in time t2' there results up until the point in time t3' a continuous transition region with an increase in pressure.

This can be led back to the through-mixing of the rinsing fluid with gas bubbles, since by way of this in the otherwise laminar flow of the rinsing fluid in the cannula 5 and in subsequent components there arises turbulences and therefore the through-flow resistance and thus the pressure rise.

At the point in time t3' the maximum pressure has been reached. On account of the reducing fluid component and thus also the turbulences or eddy formations in the gas fluid mixture from t3' there sets in a continous pressure fall until finally with a practically empty container 1 the constant pressure P3 of the gas now only flowing in the system at t6' would be achieved in the case that the means is not deactivated before this.

The ascertaining of the result that the container is empty is effected in that the reduction in pressure conveyed as electrical output signals of the unit 15 is differentiated in the unit, thus a negative gradient of the pressure is ascertained. If e.g. at t4' or where appropriate also time-delayed further over a predetermined evaluation time duration Tx to be evaluated empirically, for example 2 s until a point in time t5' it is measured and checked whether the gradient remains negative, in the unit 15 it is determied and arbitarily decided that the container 1 is empty, wherein one does not need wait whether a critical pressure limit value could have been reached, which as a precaution is provided and accommodated in the control program in order to ensure the deactivation of the means also with an disturbances at the latest on reaching this limit value. In any case normally and in the trouble-free operation the device is just deactivated at the end of the time duration Tx thus at t5' by way of closing the valve 6. Furthermore with this operating condition the valve 12 too may be closed when the container 1 is to be without pressure. After connection of a filled container the means may again be activated by opening the valves.

FIG. 3 shows qualitatively the course of the flow or gas volume flow which is acquired by the flow sensor 14 with respect to measuring technology, wherein the previously described evaluation of gas pressure and the evaluation of the flow are essentially equivalent, which is why for simplicity for the point in time and the time durations in which the respective "results" occur with the gas pressure evaluation the same reference numerals are used.

After the activation of the means at t0 the flow increases from V1 and at t1' reaches its maximum in order then in the course of the continued emptying of the container 1 to fall to the value V2 at t2'. From this point in time as already described previously in combination with FIG. 2 gas bubbles get into the cannula 5. Thereupon the flow due to the increasing flow-through resistance on account of turbulence in the rinsing fluid delivered from the container falls to a minimum at t3'. The flow then again rises when increasingly gas and finally only gas gets into the cannula 5 and would achieve, if the means are not previously deactivated, at t6' the maximum value V3' thus would exceed the predetermined limit value V4 which is also fixed as a criterium for the conclusion that the container 1 is empty and that the means at the latest is to be deactivated on reaching the value V4.

However already previously at t4' in the unit 15 by way of the signals delivered by the flow sensor 14 it is ascertained that the flow for the first time after t1' has a constantly positive gradient. If such a positive gradient is ascertained also during the evaluation time period Tx at t5' the deactivation of the means by closing the valve 6 is effected in order, with a container 1 which is now empty or declared as no longer sufficiently filled, to prevent gas from getting into the body cavity 8 via the instrument 7. Also the valve 12 with this situation may be closed if one does not wish that the container 1 remains further under pressure or gas on changing the empty container for a filled one exits from the cannula 4.

With the previously described functions of the means it is assumed to proceed from a case or operating position A in which the container 1 on deactivating the means is sufficiently filled. It may also arise that the user in a case B activates the means inadvertently with an empty container 1 which would lead to an undesired gas flow into the body cavity and is therefore be avoided. This problem to is also solved by way of the means according to the invention.

In FIG. 4 there is shown an example for the evaluation of the gas pressure for the case B at various points in time. On the pressure sensor 13 or valve 12 there is a pressure P1. On starting operation of the means by opening the valve 12, 6 at t0 the pressure falls until the point in time t7' to a minimum, which, because now the container 1 is empty lies at a lower pressure value than the pressure minimum at t1' shown in FIG. 2.

The container 1 is gradually filled with pressurised gas so that the pressure from t7' will gradually increase until at t8' a pressure equalisation is reached and the pressure in the container remains constant below the limit value P4.

In order then to be able also to acquire this operating condition for example a time duration Ty of for example 10 s beginning at t0 and ending at t9' is pregiven, which is to be dimensioned such that after completion of this time duration this pressure with the operation case B may already have a constant course. Then at t9' up to the point in time t10' there begins an evaluation time duration Tz of for example 2 s, during which it is checked whether the pressure actually further remains constant. If this is the case then at the end of the evaluation time duration Tz the means is deactivated in the manner already described previously.

Corresponding relationships with regard to the functions of the means result in the same context with a measurement of the flow with the course according to FIG. 5 shown for a case B, wherein also here it is assumed for simplification that "results" described in combination with FIG. 4 with respect to time lie as with the pressure measuring principle.

On switching on the means at to the flow rises until reaching a maximum at t7', and specifically beyond the predetermined limit value V4 which is applied as a criterium for when the container is certainly to be seen as empty.

The flow falls after the maximum with a container gradually filled with pressurised gas on account of the presure increasing with this to a value of V3 until at t8' the flow remains constant. In this case a time duration Ty beginning at t0 and ending at t10' is pregiven, from which there begins an evaluation time duration Tz ending at t10' and likewise fixed, within which it is checked whether the flow runnig above the limit value V4 remains constant in order then when it is the case to deactivate the machine.

What is claimed is:

1. An apparatus for supplying a medical instrument with rinsing fluid which is located in a container which can be put under pressure with a gas from a pressurized gas source into which two cannulas of differing lengths are inserted, comprising: a fluid conduit connectable between a longer of the cannulas and the instrument; a second valve operatively arranged in the fluid conduit; a gas conduit connectable between a shorter of the cannulas and the pressurized gas source; a first valve connected in the gas conduit between the short cannula and the gas source so that opening the first valve at a point in time t0 pressurizes the container and forces fluid from the container into the fluid conduit leading to the instrument, the second valve being closeable so as to interrupt fluid flow to the instrument, the first valve being closeable so as to interrupt the pressurized gas supply to the container; sensor means for sensing, a degree of filling of the container so that when an empty container or one which has become empty is sensed rinsing is automatically turned off, the sensor means including a pressure sensor operative to acquire a present gas pressure in the container so that in a first case A upon starting operation of a container sufficiently filled with rinsing fluid a temporal course of the gas pressure in the container can be acquired by way of the sensor and upon ascertaining a gas pressure fall during a fixed evaluation time duration Tx the apparatus is deactivated, and so that alternatively in a second case B upon starting operation of an insufficiently filled or empty container the temporal course of the gas pressure in the container can be acquired by way of the sensor and after completion of predetermined time duration Ty upon ascertaining pressure which during a fixed evaluation time duration Tz runs constant below a predetermined pressure limit value, the apparatus is deactivated; and an evaluation and control unit to which the sensor is connected, the evaluation and control unit being operative to evaluate output signals delivered by the sensor mathematically by differentiation by way of a measuring algorithm with respect to a criteria negative gradient of the gas pressure, as well as constant remaining values of the gas pressure, the evaluation and control unit then with the persistence of one of these two criteria over a respective predetermined evaluation time duration Tx or Tz being operative to control the second valve for closing or blocking the connection from the container to the instrument.

2. The apparatus according to claim 1, and further comprising an alarm device and a foot switch arranged to connect the control and evaluation unit to the alarm device so that upon starting an empty container with the foot switch the alarm device is actuated.

3. The apparatus according to claim 1, and further comprising a throttle arranged in a gas conducting branch between the pressurized air source and the short cannula, the throttle being operative to adapt flow-through resistance of the gas conducting branch to a flow-through resistance of a conducting branch beginning with the long cannula and conducting the rinsing fluid.

4. An apparatus for supplying a medical instrument with rinsing fluid which is located in a container which can be put under pressure with a gas from a pressurized gas source and into which two cannulas of differing lengths are inserted, comprising: a fluid conduit connectable between a longer of the cannulas and the instrument; a second valve operatively arranged in the fluid conduit; a gas conduit connectable between a shorter of the cannulas and the pressurized gas source; a first valve connected in the gas conduit between the sort cannula and the gas source so that opening the first valve at a point in time t0 pressurizes the container and forces fluid from the container into the fluid conduit leading to the instrument, the second valve being closeable so as to interrupt fluid flow to the instrument, the first valve being closeable so as to interrupt the pressurized gas supply to the container; sensor means for sensing a degree of filling of the container so that when an empty container or one which has become empty is sensed rinsing is automatically turned off, the sensor means including a flow sensor operative to acquire a present gas flow in the container, so that in a first case A upon starting operation of a container sufficiently filled with rinsing fluid a temporal course of the gas flow in the container can be acquired by way of the sensor and upon ascertaining a gas flow fall during a fixed evaluation time duration Tx the apparatus is deactivated, and so that alternatively in a second case B upon starting operation of an insufficiently filled or empty container the temporal course of the gas flow in the container can be acquired by way of the sensor and after completion of a predetermined time duration Ty upon ascertaining a gas flow which during a fixed evaluation time duration Tz runs constant below a predetermined flow limit value, the apparatus is deactivated; and an evaluation and control unit to which the sensor is connected, the evaluation and control unit being operative to evaluate output signals delivered by the sensor mathematically by differentiation by way of a measuring algorithm with respect to a criteria positive gradient of the gas flow as well as constant remaining values of the gas flow, the evaluation and control unit then with the persistence of one of these two criteria over a respective predetermined evaluation time duration Tx or Tz being operative to control the second valve for closing or blocking the connection from the container to the instrument.

5. The apparatus according to claim 4, and further comprising an alarm device and a foot switch arranged to connect the control and evaluation unit to the alarm device, so that upon starting an empty container with the foot switch the alarm device is actuated.

* * * * *